R. KORDES
ROSE PLANT
Filed Sept. 18, 1974
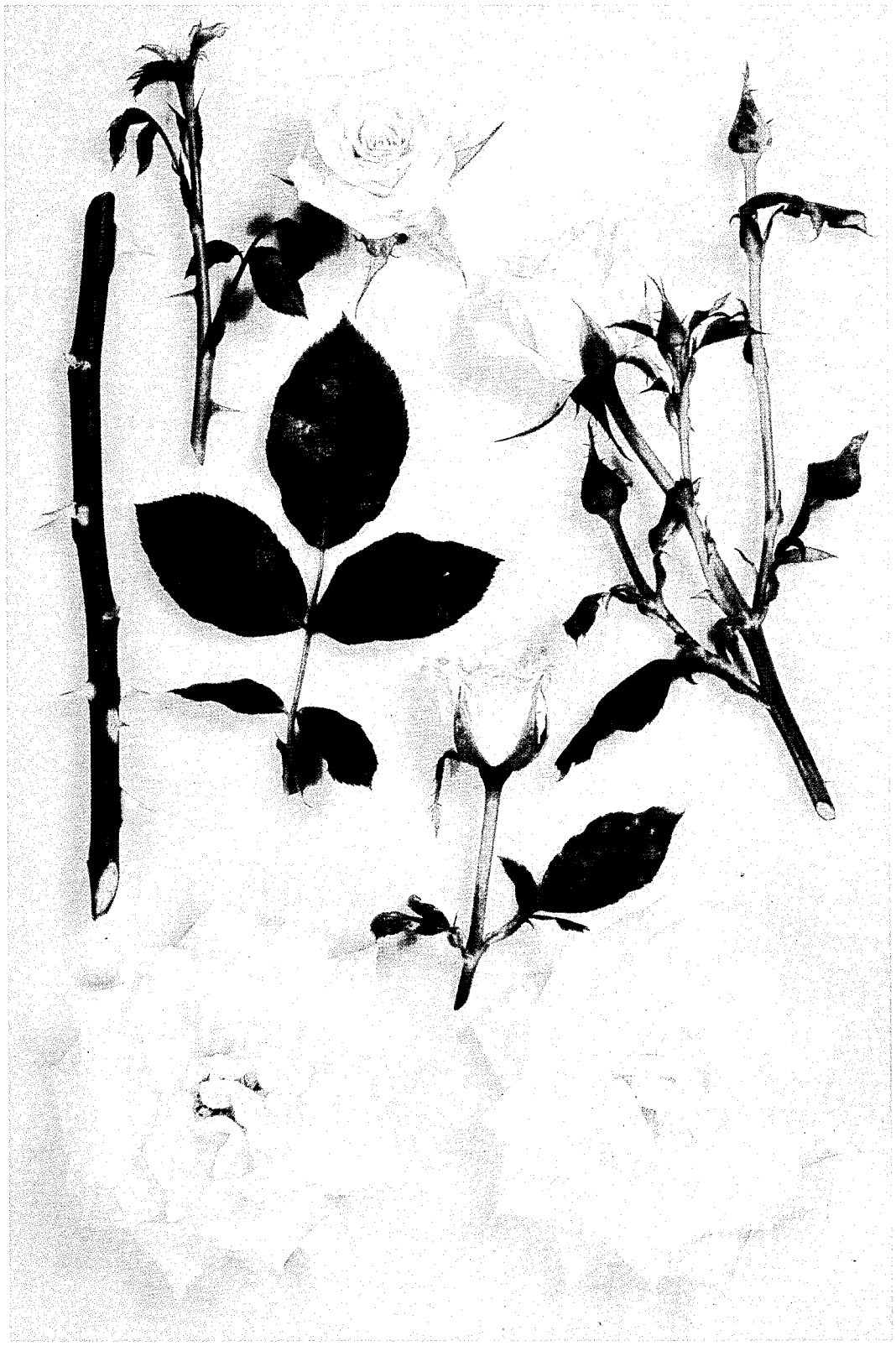

United States Patent

Plant Pat. 3,790
Patented Sept. 23, 1975

3,790
ROSE PLANT

Reimer Kordes, Sparrieshoop, near Elmshorn, Holstein, Germany, assignor to Jackson and Perkins Company, Medford, Oreg.

Filed Sept. 18, 1974, Ser. No. 507,252
Int. Cl. A01h *5/00*
U.S. Cl. Plt.—24 1 Claim

The present invention relates to a new and distinct cultivar of rose plant of the floribunda class originated by me by crossing the cultivar Mabella, U.S. Plant Pat. No. 3,228, with pollen from the cultivar Minigold, U.S. Plant Pat. No. 3,103.

The primary objective of this breeding was to produce a new and improved cultivar of the floribunda class bearing yellow buds on stems suitable for cut flowers with improved substance (stiffness) in the petals and a good color holding ability.

This objective was fully achieved along with other desirable improvements as evidenced by the following unique combination of characteristics which are outstanding in the new cultivar and which distinguish it from its parents as well as from all other cultivars of which I am aware:

1. A very vigorous plant.
2. Heavy, strong stems similar to the cultivar Mabella.
3. Flower buds smaller than those of Mabella, near the size of those of Minigold but of a slightly deeper yellow color and fewer petals.
4. Petals of stiff, heavy substance.
5. Flowers borne in large clusters on terminals of main basal branches but borne generally singly on lateral branches used for cut flowers resulting in little "disbudding" being required.
6. Little fragrance.

Asexual reproduction of this new cultivar by budding as performed at Sparrieshoop, West Germany, and at Irvine, Calif., shows that the aforementioned characteristics come true to form and are established and transmitted through succeeding propagations.

The accompanying illustration shows typical specimens of the vegetative growth and flowers of this new cultivar in different stages of development and as depicted in color as nearly true as it is reasonably possible to make the same in a color illustration of this character.

The following is a detailed description of my new rose variety with color terminology in accordance with Wilson's Horticultural Color Chart, except where ordinary dictionary significance of color is indicated.

Parentage: Seedling.
*Seed parent.*—Mabella, U.S. Plant Pat. No. 3,228.
*Pollen parent.*—Minigold, U.S. Plant Pat. No. 3,103.
Classification:
*Botanic.*—Rosa hybrid.
*Commercial.*—Floribunda.

FLOWER

Observations were made at Irvine, Calif., in August from plants grown in a greenhouse.

Blooming habit: Recurrent—continuous.
Bud:
*Size.*—1 inch when petals start to unfurl.
*Form.*—Blunt top, ovoid.
*Color.*—When sepals first divide Buttercup Yellow (5/1) with occasional streaks on the outer petal of a color near Spanish Orange (010). When half blown; upper side of petals near Chrome Yellow (605). Lower side of petals near Chrome Yellow (605/1).
*Sepals.*—Color: Outer surface near Scheeles Green (860/3) with many small stipitate glands scattered over the surface. Inner surface near Scheeles Green (860/3) covered lightly with white tomentum. Three appendaged sepals lightly appendaged. Two unappendaged sepals hairy edged.

*Receptacle.*—Color: Near Scheeles Green (860/3). Shape: Funnel. Size: Broad. Surface: Smooth.
*Peduncle.*—Length: Medium to short. Surface: Glandular with many stipitate glands. Color: Light green. Strength: Stiff and erect.
*Opening.*—Spiral with petals slightly pointed.
Bloom:
*Size.*—Medium. Average open size 3 inches.
*Borne.*—Singly, and in flat clusters.
*Stems.*—Medium, strong.
*Form.*—When first open—high centered. Permanence—outer petal edges slightly curl.
*Color.*—Center of flowers: Upper side of petals near Buttercup Yellow (5/1). Reverse side of petas near Empire Yellow (603). Base of petals same as balance of petals. General tonality from a distance for freshly opened flowers near Buttercup Yellow (5/1). Variegations: as indicated in bud description.
*Discoloration.*—At end of first day—near Buttercup Yellow (5/1). Third day—near Empire Yellow (603/1).
*Fragrance.*—Slight.
*Petals.*—Texture: Thick.
*Shape.*—Near round.
*Form.*—Edges slighly quilled.
*Arrangement.*—Imbricated.
*Petaloids in center.*—Few.
*Persistence.*—Hang on and dry.
*Lastingness.*—On the plant—very long. As cut flower—very long.
Reproductive parts:
*Anthers.*—Medium. Color—Majolica Yellow (09). Arrangement—regular around styles.
*Filaments.*—Color—yellow.
*Pollen.*—Gold yellow.
*Styles.*—Color—near white.
*Stigmas.*—Color—light yellow.

PLANT

Form: Bush.
Growth: Very vigorous, upright, branching.
Foliage: Number of leaflets on normal mid-stem leaves, 5.
*Size.*—Medium.
*Quantity.*—Normal.
*Color.*—New foliage: near Garnet Brown (00918/3). Old foliage: near Spinach Green (0960).
Leaflets:
*Shape.*—Oval.
*Texture.*—Leathery.
*Edge.*—Serrated.
*Serration.*—Single, small.
*Petiole.* — Rachis—Color—Green. Underside—few prickles.
*Stipules.*—Medium, bearded.
*Disease resistance.*—Slightly susceptible to mildew under normal growing conditions at Irvine, Calif.
Wood:
*New wood.*—Color—light green. Bark—smooth.
*Old wood.*—Color—green. Bark—smooth.
Prickles:
*Quantity.*—On main stalks from base—ordinary. On laterals from stalk—ordinary.
*Form.*—Broad based, long, straight.
*Color when young.*—Brown.
*Position.*—Irregular.

Small prickles:

*Quantity.*—On main stalks—few. On laterals—few.
*Color.*—Brown.

I claim:

1. A new and improved rose plant of the floribunda class substantially as illustrated and described, and characterized particularly by its vigorous growth with heavy, strong stems similar to those of the cultivar Mabella, with buds near those of Minigold, but of a deeper yellow color and fewer petals, with flowers having petals of stiff, heavy substance and borne in large clusters on terminals of main basal branches, but generally singly on lateral branches, and little fragrance.

No references cited.

ROBERT E. BAGWILL, Primary Examiner